United States Patent
Wang et al.

(10) Patent No.: US 6,168,748 B1
(45) Date of Patent: *Jan. 2, 2001

(54) METHOD OF BALLOON FORMATION BY COLD DRAWING/NECKING

(75) Inventors: Lixiao Wang, Maple Grove; Jianhua Chen; Nao Lee, both of Brooklyn Park; Daniel J. Horn, Shoreview, all of MN (US)

(73) Assignee: SciMed life Systems, Inc., Maple Grove, MN (US)

(*) Notice: Under 35 U.S.C. 154(b), the term of this patent shall be extended for 0 days.

This patent is subject to a terminal disclaimer.

(21) Appl. No.: 09/152,413

(22) Filed: Sep. 14, 1998

Related U.S. Application Data

(63) Continuation of application No. 08/954,453, filed on Sep. 20, 1997, now Pat. No. 5,807,520, which is a continuation of application No. 08/555,219, filed on Nov. 8, 1995, now abandoned, which is a continuation-in-part of application No. 08/397,837, filed on Mar. 2, 1995, now Pat. No. 5,556,383.

(51) Int. Cl.[7] .................... B29C 49/08; A61M 29/00
(52) U.S. Cl. .................... 264/520; 264/521; 264/529; 264/532; 264/573; 264/291; 264/292; 604/96; 606/194
(58) Field of Search ................ 264/520, 529, 264/532, 521, 573, 291, 292; 604/96; 606/194

(56) References Cited

U.S. PATENT DOCUMENTS

| | | | |
|---|---|---|---|
| 5,156,612 | * 10/1992 | Pinchuk et al. | 606/194 |
| 5,807,520 | * 9/1998 | Wang et al. | 264/520 |
| 5,865,721 | * 2/1999 | Andrews et al. | 604/96 |
| 5,951,941 | * 9/1999 | Wang et al. | 264/523 |

* cited by examiner

Primary Examiner—Jan H. Silbaugh
Assistant Examiner—Suzanne E. McDowell
(74) Attorney, Agent, or Firm—Vidas, Arrett & Steinkraus

(57) ABSTRACT

A method for forming a balloon for a dilatation catheter involving the steps of extruding a segment of thermoplastic material, maintaining the center portion at a temperature below the glass transition of the thermoplastic material, drawing the segment to a predetermined length, wherein after the drawing the wall thickness of the center portion does not appreciably change, and expanding the segment in a mold to produce the balloon.

24 Claims, 5 Drawing Sheets

METHOD OF BALLOON FORMATION BY COLD DRAWING/NECKING

This application is a continuation of U.S. application Ser. No. 08/954,453, filed Sep. 20, 1997, now U.S. Pat. No. 5,807,520, which is a continuation of U.S. application Ser. No. 08/555,219, filed Nov. 8, 1995, now abandoned, both of which are incorporated herein by reference in their entirety. U.S. application Ser. No. 08/555,219, in turn, is a continuation-in-part of application Ser. No. 08/397,837, filed Mar. 2, 1995, now U.S. Pat. No. 5,556,383.

BACKGROUND OF THE INVENTION

The present invention relates to a method for making balloons for catheters used in medical dilatation procedures.

Balloon catheters are being used extensively in procedures related to the treatment of blood vessels. For example, arterial stenosis is commonly treated by angioplasty procedures which involve inserting balloon catheters into specific arteries. Balloon catheters have also been found useful in procedures involving dilation of body cavities.

The most widely used form of angioplasty makes use of a dilatation catheter which has an inflatable balloon at its distal end. Using fluoroscopy, a physician guides the catheter through the vascular system until the balloon is positioned across the stenoses. The balloon is then inflated by supplying liquid under pressure through an inflation lumen to the balloon. The inflation of the balloon causes stretching of a blood vessel and pressing of the lesion into the blood vessel wall to reestablish acceptable blood flow through the blood vessel.

In order to treat very tight stenoses with small openings, there has been a continuing effort to reduce the profile of the catheter so that the catheter can reach and pass through the small opening of the stenoses. There has also been an effort to reduce the profile of the catheter after an initial use and deflation of the balloon to permit passage of the catheter through additional lesions that are to be treated or to allow entry and retreatment of lesions that reclose after initial treatment.

One factor manipulated to reduce the profile of the dilatation catheter is the wall thickness of the balloon material. Balloons for dilatation balloon catheters have been made from a wide variety of polymeric materials. Typically the balloon wall thicknesses have been on the order of 0.0003 to 0.003 inches for most materials. There have been continuing efforts, however, to develop ever thinner walled balloon materials, while still retaining the necessary distensibility and burst pressure rating, so as to permit lower deflated profiles.

The profile of the deflated balloon is also limited by the thickness of the waist and cone portions of the balloon. Usually, the waist and cone wall thicknesses are thicker than that of the body of the balloon due to the smaller diameter of the waist and cone portions. In order to reduce the overall profile of the deflated balloon, reduction of the wall thickness of the waist and cone portions must be addressed.

It is possible to make balloons from a variety of materials that are generally of the thermoplastic polymeric type. Such materials may include: polyethylenes, ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; silicone-polycarbonate copolymers; polyamides; and ethylene-vinyl acetate copolymers. Orientable polyesters, especially polyethylene terephthalate (PET), are among the preferred materials for forming catheter balloons. References illustrating the materials and methods of making catheter balloons include: U.S. Pat. No. 4,413,989 and U.S. Pat. No. 4,456,000 to Schjeldahl et al, U.S. Pat. No. 4,490,421, U.S. Pat. No. Re 32,983 and U.S. Pat. No. Re 33,561 to Levy, and U.S. Pat. No. 4,906,244; U.S. Pat. No. 5,108,415 and U.S. Pat. No. 5,156,612 to Pinchuck et al.

High tensile strengths and uniformity of wall thickness are important in angioplasty balloons because they allow for the use of high pressure in a balloon having a relatively thin wall thickness. High pressure is often needed to treat some forms of stenosis. Thin and uniform wall thicknesses enable the deflated balloon to remain narrow, making it easier to advance the balloon through the arterial system.

Prior art balloon forming techniques involve stretching and blowing of the balloon from a segment of extruded polymer tubing. Balloons produced by stretching and blowing a tubular preform or "parison" typically have much thicker waist and cone walls than the wall thickness of their body portions. The thicker cone walls contribute to the overall thickness of the catheter, making tracking, crossing and recrossing of lesions more difficult. Further, thick cones interfere with refolding of the balloon on deflation so that the deflated balloon can only be further inserted or withdrawn with difficulty, occasionally even damaging the blood vessel.

There have been several solutions proposed for reducing the cone or waist thickness of catheter balloons in U.S. Pat. No. 4,906,241, U.S. Pat. No. 4,963,313, U.S. Pat. No. 5,304,340, U.S. Pat. No. 5,087,394, EP 318,919, EP 485,903. However, the procedures involved in these references are quite cumbersome and so it is desirable that simplified methods be developed to provide cone and waist walls with reduced, uniform thicknesses.

EP 318,919 to Noddin et al. discloses a procedure in which a portion of the tube is crystallized to render it dimensionally stable under heated conditions. The portion stabilized can not be appreciably inflated or drawn. The tube is heated in a heated bath and as one end is secured in place the other is drawn to a desired length and in the process is necked-down. The tube is drawn down to a constant diameter sleeve. After the initial necking-down of the tube, the tube is reversed in the bath and the second necked-down portion is formed by the same procedure. After the preform is complete the tube is submerged horizontally and restrained at both ends. Two conical portions at opposing ends are arranged to define the shape of the tapered sections of the balloon. Simultaneously the tube is drawn and expanded without constraint until the molecules of the wall material in the balloon region become stabilized in a biaxially oriented condition. The portions of the tube having the preform tapers expand until they are constrained to the shape of the constraining cones.

U.S. Pat. No. 5,087,394 discloses a method of forming a balloon wherein a length of polymer tubing is formed by drawing the tubing material from an extruder using an extruder die and then irradiated. The stretching method involves positioning an internal support mandrel within the tubing and compressing a portion of the intermediate segment onto the mandrel with a body clamp. The end segment is heated and stretched longitudinally to the desired length. The process of pulling the tube through a restricted hot die or body clamp forms the necked portions and thin waist segments. The other end segment is optionally stretched in a similar manner. The tubing is then heated, radially stretched by blow-molding to define the balloon and cooled.

EP 485,903 describes a method wherein a tubular parison is formed of a drawable or orientable polymer. It is heated in a metal mold in the range from the second-order transition temperature to the first-order transition temperature of the polymer used. The parison is stretched in the direction of its axis and then inflated radially resulting in a biaxially-drawn or biaxially oriented crude balloon. The parison is then cooled below the second-order transition temperature and deflated. The tapered portions of the crude balloon are redrawn by stretching to reduce their wall thicknesses. The balloon is inflated again and heated above the second transition temperature and then cooled.

The Levy patents, teach first drawing the tubing by axially pulling the tube in a uniform manner apart and then expanding the tube with fluid in a confining apparatus. The stretch process occurs at a temperature above the glass transition temperature and below the melting temperature of the tubing material.

There remains, however, a need to continue to improve balloon wall strengths while simultaneously reducing their wall thickness and maintaining uniformity. The present invention addresses these needs by reducing the wall thickness of cone and waist portions and by minimizing protruding bumps and distortions during folding of the balloon and wrapping around the catheter shaft. The resulting balloon is smaller in size for easier insertion into the body lumen.

SUMMARY OF THE INVENTION

The present invention in one aspect is a method for forming a balloon for a dilatation catheter involving the steps of extruding a segment of thermoplastic material, maintaining the center portion at a temperature below the glass transition temperature (Tg) of the thermoplastic material so that it remains dimensionally stable and cannot be appreciably drawn, drawing the segment to a predetermined length, wherein after the drawing the wall thickness of the center portion does not substantially change, and expanding the segment in a mold to produce the balloon. Maintaining the center portion at a temperature below the Tg of the thermoplastic material prevents it from stretching axially, thus allowing it to maintain its thickness. Only during the expansion phase do the center portion walls thin due to the radial pressure. The resulting stretched portion on either side of the center portion form the waist and part of the cone portions. Due to the target stretching of the present invention, the resulting waist and cone portions have reduced wall thickness, thus reducing the balloon profile.

The blowing step of forming the balloon for a catheter, comprises placing the tubing of a thermoplastic material in a mold and blowing the balloon by pressurizing and tensioning the tubing and gradually dipping the mold into a heated transfer media so as to sequentially blow the first waist, the body and the second waist portions of the balloon, the tubing being subjected to a relatively lower pressure, and preferably a relatively a lower tension, while the body portion is blown than while the first and second waist portions are blown. The variance in the thickness of balloon cones and waists can be further improved during the blowing process by varying the axial tension and blowing pressure at several stages as the mold containing the balloon preform is dipped into a heating medium.

DETAILED DESCRIPTION OF THE PREFERRED EMBODIMENTS

Figure 1:
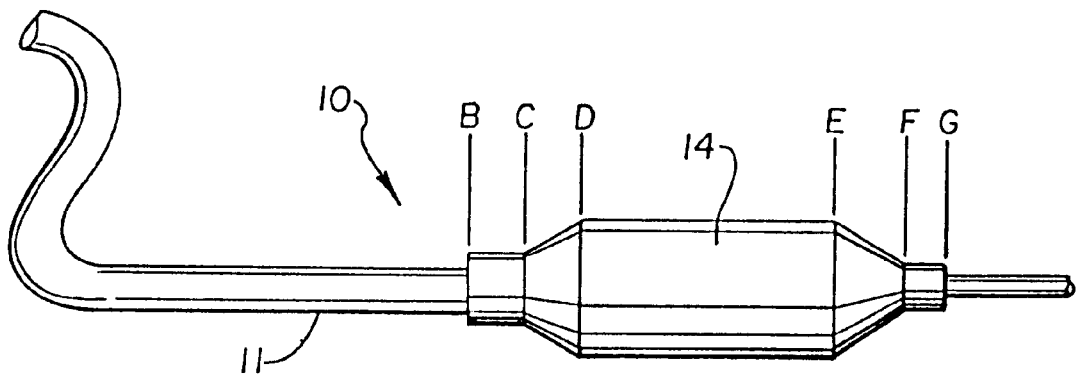
FIG. 1 is a perspective view of an angioplasty catheter having an example of a balloon fabricated from the inventive method mounted thereon.

The dilatation balloon fabricated by the present inventive method illustrated generally at 10 in FIG. 1, includes an inflatable balloon 14 mounted at the distal end of an elongated flexible shaft 11. Catheter 10 is conventional in its construction, providing a lumen communicating with the interior of balloon 14, for inflation and deflation of the balloon, and other optional features conventional in the dilatation catheter art. The balloon 14 is in its inflated configuration. The balloon 14 is formed of a thermoplastic polymer material which provides the balloon with its essential compliance characteristics. It may be any thermoplastic polymer suitable for use as an angioplasty balloon material. Preferred materials include thermoplastic elastomers, suitably, polyamide elastomers, such as Pebax® 7233, 7033, or 6333, polyester/polyether elastomers such as Arnitel EM 740 (DSM Engineering), and polyurethane elastomers such as Pellethane 2102-80D. Other thermoplastic materials such as PET, Surlyn® (polyethylene ionomer), nylon, ethylene-vinyl acetate or those previously described for catheter balloons may be employed. Most advantageously the balloon material is Pebax 7033 (Atochem, Pa.) or PET.

Figure 2A:
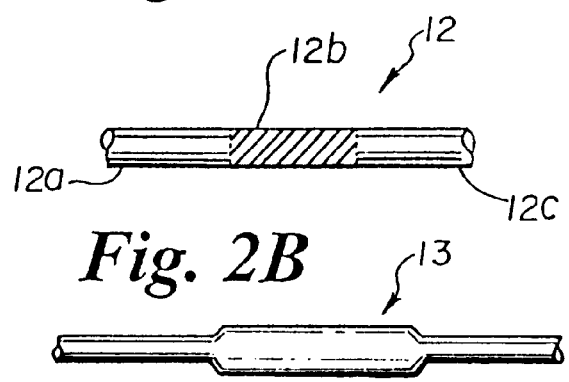
FIGS. 2a, 2b and 2c illustrate the results of various process steps in forming a catheter balloon, depicting respectively, side elevational views of an extruded tube of polymer material used to form the balloon, a stretched polymer tubing preform prepared from the extruded tube, and a formed balloon prepared from the stretched polymer tubing preform.
Figure 2B:
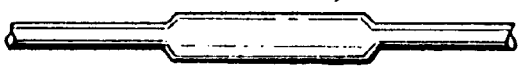
Figure 2C:
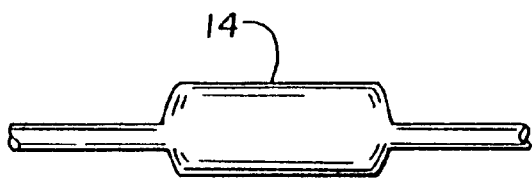

The method of the invention is performed by extruding tubing of a thermoplastic polymer. Any conventional extruder may be employed to perform the extrusion process. After the extrusion, the center portion 12b of the polymer tubing, which eventually becomes the balloon, is maintained at a temperature below the tubing's glass transition temperature as described in more detail below. At this point the polymer tubing has three sections, a proximal end 12a, a distal end 12c and a center portion 12b. The polymer tubing is then prestretched on either side of the center portion 12b by elongating the proximal 12a and distal 12c ends axially. Referring to FIGS. 2a–2c, the prestretching process comprises applying an axial stretching force to the extruded polymer tubing 12, allowing the extruded polymer tubing to stretch while maintaining the axial stretching force and finally allowing the stretched polymer tubing 13 to reach approximately room temperature. Once the prestretch is complete, the stretched polymer tubing 13 is radially expanded into the form of a balloon 14 by using a molding process. The molding process comprises placing the stretched polymer tubing 13 in a mold, heating the mold and expanding the stretched polymer tubing radially by means of internal pressure. After sufficient time has passed for the balloon to form, the mold is cooled and the balloon 14 is removed.

Figure 3:
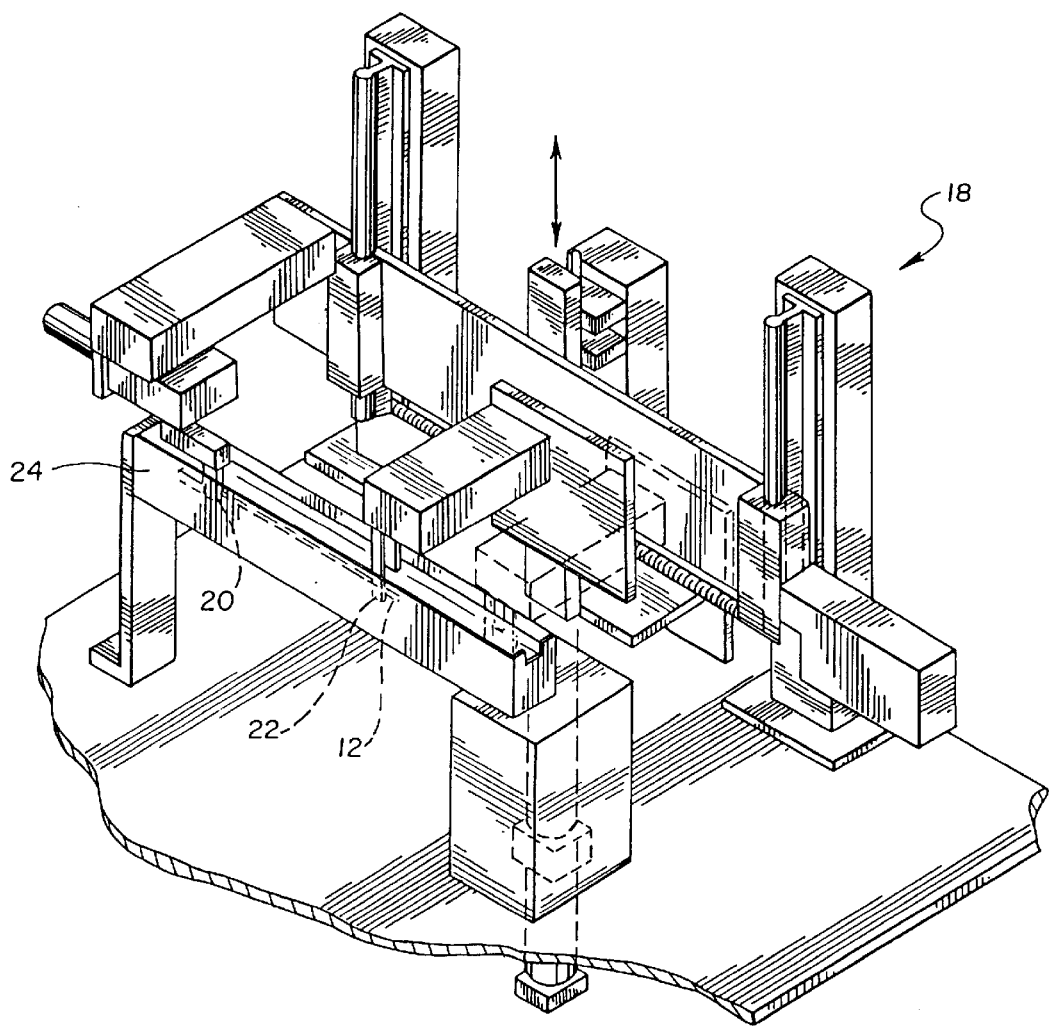
FIG. 3 is a schematic view of a stretching device that may be useful in practicing the method of the invention.

The cold drawing prestretch step stretches the section of a cut length of polymer tubing from the extrusion to a predetermined length at a specific rate. Desirably, the stretching temperature is set just prior to stretching. FIG. 3 illustrates one device useful in performing the prestretch. The device 18 of FIG. 3 possesses two jaws 20 and 22 capable of gripping at least one cut length of extruded polymer tubing 12. The appropriate temperature, which is defined by the method and described below, is established. The first gripping jaw 20 may remain stationary while the second gripping jaw 22 moves horizontally at a set rate to a predetermined final position, thereby achieving the desired final stretch. The stretch ratio is calculated by dividing the final length of the stretched section of polymer tubing (the portion between jaws 20 and 22) by the initial length of that section.

After the proximal and distal ends 12a & 12c of the polymer tubing 12 are stretched to the desired stretch ratio and length, the ends are allowed to cool. The stretched polymer tubing 13 may then be moved to a water bath (not shown), preferably maintained at room temperature. During this process, the stretched polymer tubing portion 13 of polymer tubing 12 is held on both ends in order to apply sufficient tension to ensure that the polymer tubing does not relax and shrink or recover from the stretch.

The methods and conditions of cold drawing are discussed below. The basic objective is to maintain the center portion 12b as shown in FIG. 2a at a temperature below the Tg, or below the maximum Tg if the material has multiple Tg's, of the tubing material and then to draw the polymer tubing. This is to assure that only the ends are drawn and not the center portion. The temperature of the center portion 12b may be maintained by isolating the center portion 12b so it remains below the Tg, cooling the center portion 12b of the tubing before stretching, cooling the entire segment of tubing or positioning cold clamps on the center portion. During the stretching process, the polymer tube is drawn through a neck, the undrawn material being transformed gradually into drawn materials with a constant reduction in cross-section as it passes through the newly formed neck portion propagating toward the center portion. Cold drawing allows the necks to be formed without die or clamp restriction as disclosed in the prior art. Maintaining the desired temperature of the center portion 12b acts to restrain the center portion 12b and promotes a substantial transition in thickness causing molecular alignment and changes in morphology for both crystalline and amorphous polymers.

Figure 7:
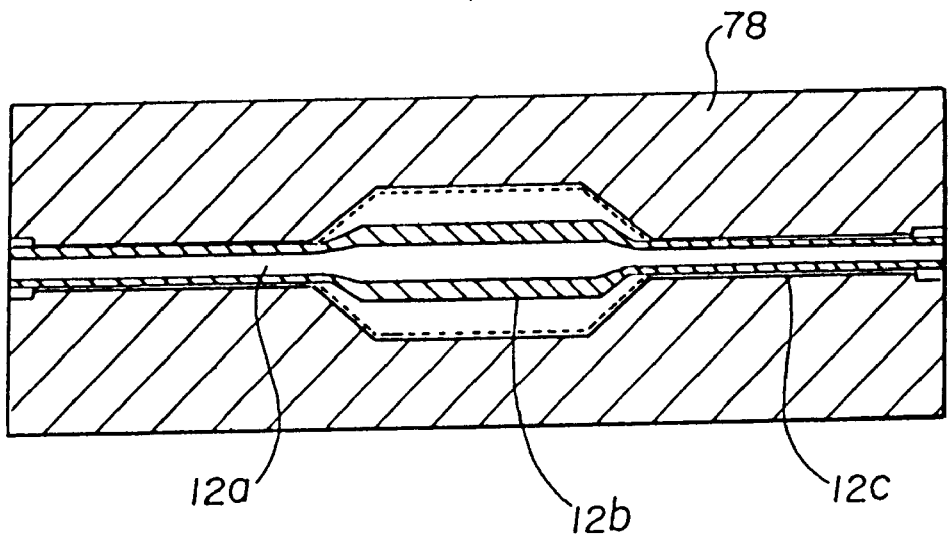
FIG. 7 is a side view of a drawn or stretched segment of tubing within a mold before the molding process.

The stretching process can occur under a number of conditions as long as the center portion remains below the Tg temperature. In one embodiment the center portion 12b of the extruded polymer tubing is cooled by dipping the center portion 12b and the distal portion 12c of the tubing into a cold water bath and drawing the proximal portion 12a to a desirable length and then removing the tubing from the water bath and turning the tubing over and dipping the proximal portion 12a and the center portion 12b into the cold water bath and drawing the distal portion 12c to a desirable length. In another embodiment, the same effect is achieved by holding the center portion 12b in place with cold clamps, thereby maintaining the center portion 12b at a low temperature during the drawing step. While the center portion of the polymer tubing is maintained at a temperature below the glass transition temperature of the extruded polymer tubing 12 it is gradually drawn apart. A suitable temperature is the range extending from −178° C. to +70° C. and is below the Tg of the polymer material or the maximum Tg if the polymer material comprises block copolymers. However, the preferred temperature being in the range of −100° C. to −20° C. (+/−5° C.). Preferably, but not required, for block copolymers the temperature is below the lowest Tg. The stretch rate may be in the range between 25%–75% per second. The preferred rate of stretching is 75% per second. The desired amount of axial elongation prior to radial expansion is in the range of 200% to 500%. Preferably, however, the axial elongation occurring in this phase is 280%. The tubing is then allowed to reach approximately room temperature. The resulting tubing has a varied wall thickness as shown in FIG. 7 which shows a drawn segment of tubing inside a mold 78, wherein the center portion 12b substantially maintains its original thickness and gradually thins out toward the ends 12a and 12c to a substantially constant smaller thickness. After the polymer tubing assumes a workable temperature it is transferred to the molding process.

An alternative method for tubing made from highly orientable material, such as PET or nylon, is performed by cooling the entire extruded polymer tubing below the glass transition temperature of the tubing material. If the Tg of the material is above room temperature cooling may not be necessary. The targeted temperature is dictated by the type of material used. The tubing is then gradually drawn apart. As this is done, the walls of the tubing thin out from the ends gradually toward the center, slowly decreasing the length of the center portion 12b until the desired length is reached. The tubing is then allowed to reach approximately room temperature.

Under conventional conditions when the specimen is extended, occasionally a considerable rise of temperature occurs in the region of the neck, however, the increase in temperature is small at slow rates and therefore can be controlled to prevent overheating of the central portion 12b.

The method of cold drawing at lower temperatures described herein gives sharper and more favorable neck transition. The resulting tubing has a varied wall thickness as shown in FIG. 7, wherein the center portion 12b maintains its original thickness and gradually thins out toward the ends to a substantially constant smaller thickness. The necked portions form the waists and part of the cones of the balloon at the proximal end and distal end and the unnecked portion forms the balloon body. As shown in FIG. 7, the center portion 12b is approximately the length of the balloon portion of the mold before the blowing. Alternatively, the center portion 12b may be drawn so that it is shorter than the balloon portion of the mold and then eventually extended out to fill out the mold after the blowing process.

Figure 4:
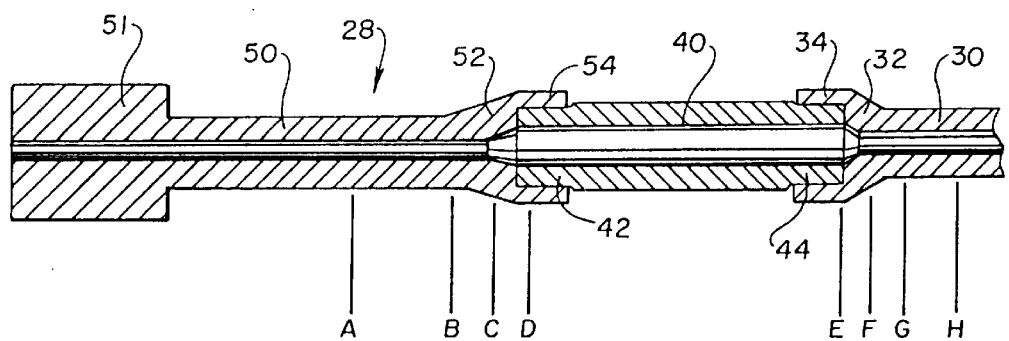
FIG. 4 is a cross-sectional view of a preferred mold used in the method of the invention.

After the prestretch process the stretched polymer tubing 13 is expanded radially using internal pressure. The dimensions to which it is stretched are preferably controlled by performing the radial stretching while the polymer tubing 13 is in a mold having the shape of the desired balloon. A suitable mold 28 is shown in FIG. 4. Heating the stretched polymer tubing 13 while radially expanding it may best be accomplished by dipping the mold 28 into hot water while internal pressure is applied. Various tensions and pressures are used in the distal, body and proximal portions. Preferably, low tensions and low pressures are used in the body portion to maintain the right wall thickness and maximize consistent burst pressure.

To perform the radial expansion step, one end of the stretched polymer tubing inside of the area where it was gripped by jaws 20 and 22 is cut off to provide an opening to the lumen of the polymer tubing 13. The stretched polymer tubing 13 is then fed through the mold 28 which consists of three parts: the proximal portion (top) 30, the body 40 and the distal (bottom) portion 50. These three sections fit tightly together and provide the polymer tubing 13 a form to blow to.

Figure 5:
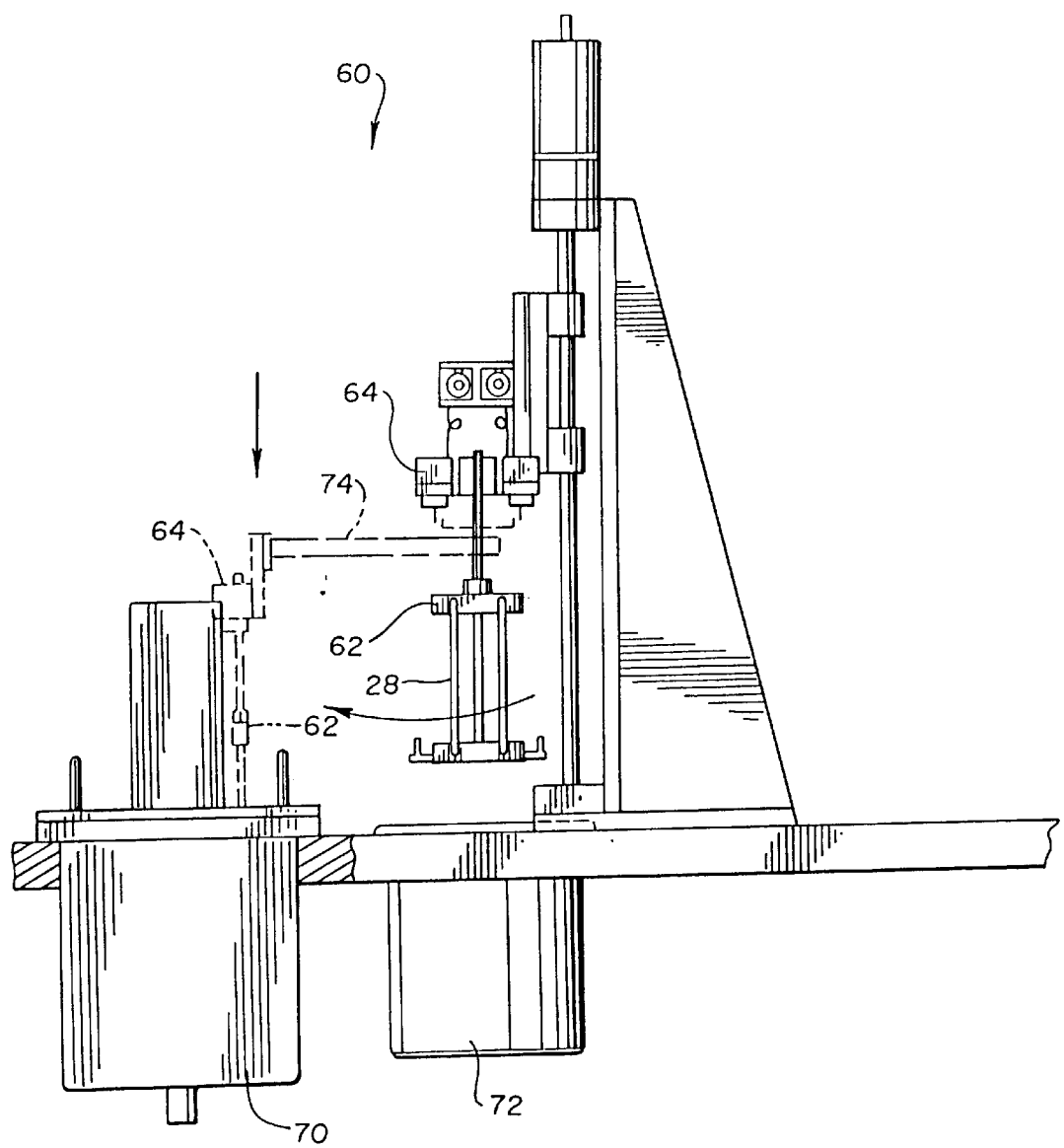
FIG. 5 is a side elevation view of a molding station that may be useful in practicing the method of the invention.

Referring to FIG. 4, the distal portion 50 of the preferred mold 28 is generally between 0.6 and 1.4 inches long, which includes the enlarged end section 51 used to hold the mold 28 in the molding fixture 62 (FIG. 5). The distal cone section 52 is formed at an angle of between 15° and 45° with the axis of the mold 28. The cup 54 of the distal portion, which interfaces with the distal insert portion 42 of body 40, generally has a length of 0.120 inches. The proximal portion 30 of the preferred mold 28 is generally between 1.1 and 2.0 inches long. The proximal cone section 32 is also formed at an angle of between 15° and 45° with the axis of the mold 28. The cup 34 of the proximal portion interfaces with the proximal insert portion 44, symmetrical with the distal insert mold portion 42 of body 40. The length for the balloon body 40 is generally between 0.4 and 2 inches long. The inner and outer diameter of the mold sections 30, 40 and 50, and the angles of each cone 32, 52 are both dependent on the desired balloon size. The mold 28 for the balloon will be different when producing different sized balloons, which is necessary to meet the preference or needs of those who will perform medical treatments with the balloon.

Figure 6:
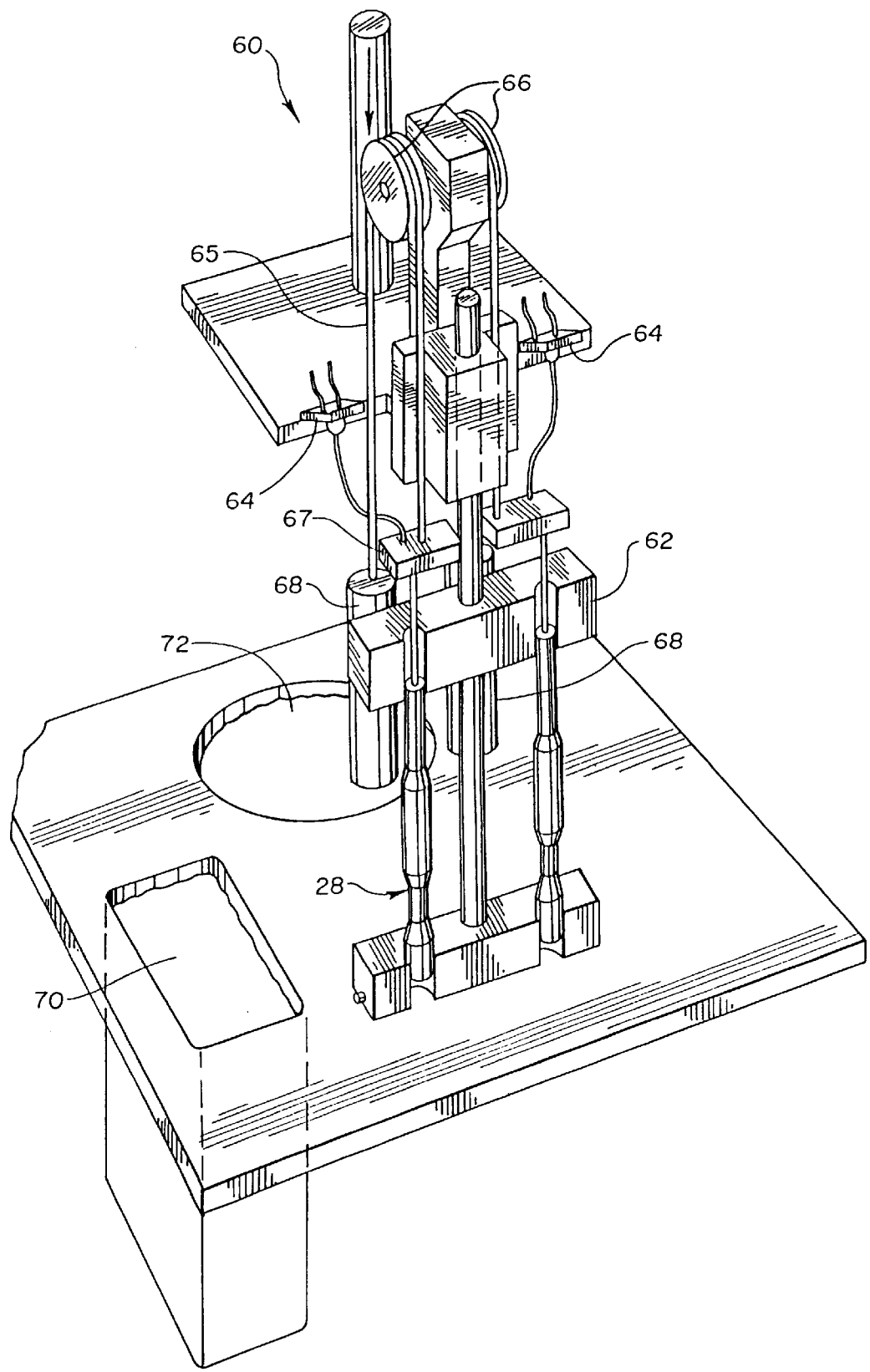
FIG. 6 is a perspective schematic representation of relevant portions of the molding station of FIG. 5.

The molds 28 of the present invention are preferably made of 303 stainless steel with a smooth mirror finish to provide a smooth finish on the balloon surface. The appropriate mold 28, with the stretched polymer tubing 13 inside, may be heated while pressure is applied using a device 60 such as the one depicted in FIGS. 5 and 6. With this device 60, the mold 28 is placed in a holder 62. The polymer tubing 13 extends out from the top of the mold 28 and is fed into a Touhy clamp 64 through which a pressurized fluid, preferably nitrogen gas, is applied to the inner lumen of the polymer tubing 13. The tubing at the bottom of the mold 28 is clamped off such that no gas can flow through it. The pressure applied is suitably in the range of 100–700 psi.

One advantage of using a device 60 is that tension may be applied to the polymer tubing 13 during the molding phase. A string 65 trained over pulley 66 (shown in FIG. 6 but deleted from FIG. 5 for sake of clarity) may be attached to a tension clamp 67 adjacent the Touhy clamp 64. The tension clamp 67 holds the polymer tubing 13 to apply tension to it without closing off the flow path of pressurized fluid into polymer tubing 13. Weights 68 attached to the end of string 65 may thus provide tension to the polymer tubing 13. Alternatively, the pressure may be applied by a computer controlled pneumatic cylinder for highly accurate measurements. Generally, 0–700 g of tension may be applied. Tension may be applied during the molding process to better control the wall thickness of certain areas of the balloon, primarily the waist sections. The tension decreases the cross sectional area of the balloon waists, thereby increasing flexibility in those regions.

The polymer tubing 13, subjected to specific interior pressures, is then heated. As depicted by dashed lines in FIG. 5, the mold 28 is dipped into a water bath 70, suitably at a rate of 4 mm/sec., with the total process of submerging the mold 2.3 inches into the bath 70 taking approximately 15 seconds. Preferably, the bath 70 is a hot water bath maintained at a temperature range of 85–98° C., with 95° C. (+/−0.4° C.) being the most preferred temperature. Once the entire mold 28 has been submerged it is held stationary for a period of time, suitably 40 seconds, while the balloon and waist portions yield completely and stabilize. The radial expansion, or hoop ratio (calculated by dividing the inner diameter of the balloon by the inner diameter of the extruded tubing), should be in the range of 4–9. However, the preferred hoop ratio for PET is approximately 8.0 and for Pebax is approximately 6.0. A lower hoop ratio may result in compliance which is higher than desired. A higher hoop ratio may result in preforms which will not blow out fully. During this phase of radial expansion, the polymer tubing 13 is slightly elongated.

In accordance with a further aspect of the invention the stretched polymer tubing 13 is blown during a programmed dipping cycle, for dipping into hot water bath 70, during which the pressure and axial tension are varied at several stages so that the balloon is sequentially blown from one end to the other (proximal, body and distal, or vice versa). By this method, a further reduced waist and cone thickness is obtained.

FIG. 4 has been labeled to show depth regions at which transitions of pressure and/or tension occur in this aspect of the invention as mold 28 is dipped into bath 70. Corresponding locations on the balloon 14 are labeled in FIG. 1. The region B-C comprises the proximal waist portion, the region C-D comprises the proximal cone portion, the region D-E comprises the body portion, the region E-F comprises the distal cone portion and the region F-G comprises the distal waist portion of the mold. The balloon blowing process of the invention involves the steps of:

pressurizing the stretched tubing to a first pressure in the range of 150–500 psi and applying a first tension in the range of 5–500 g;

dipping the mold to a first depth in the range of from the transition (C) from the first waist to the first cone to the transition (D) from the first cone to the body portion of the balloon;

reducing the pressure to a second pressure between 80 and 170 psi and setting a second tension in the range of the first tension;

dipping the mold to a second depth in the range of from the transition (E) from the body portion to the second cone portion to the transition (F) from the second cone to the second waist;

increasing the pressure to a third pressure higher than the second pressure and between 150 and 500 psi and increasing the tension to a third tension, higher than the first and second tensions, and then, dipping the mold to a third depth (H) beyond the depth (G) of the second waist.

Although the process may be accomplished with substantially continuous dipping, it is preferred that the mold be held at each of the first, second and third depths for predetermined time intervals before changing pressure/tension parameters and moving to the next depth. Suitable hold time intervals are between 1 and 40 seconds at the first depth, between 1 and 40 seconds at the second depth and between 10 and 100 seconds at the third depth. For example, a typical dipping program for a PET polymer balloon, beginning at an initial depth (A) before the depth (B) of the first waist of the balloon, and using a 95° C. hot water bath as heating media, will take a total of approximately 60–90 seconds.

The third tension is suitably in the range of 50 to 700 g, and is higher than the second tension, suitably higher than both the first and second tensions. For balloons of 4.00 mm diameter or less, the third tension will usually not exceed 700 g. The second tension may be the same or different from the first tension and if different will usually be less than the first tension. In general the tension employed at all depths will be higher as the diameter of the balloon is increased. For balloons having nominal diameters of at least 2.25 mm it is preferred that the third tension be higher than both the first and second tensions by at least 150 grams and at all typical angioplasty balloon diameters it is preferred that the difference between the second and third pressures be at least 100 psi, usually at least 150 psi.

It should be noted that this aspect of the invention can also be practiced by inserting the end of mold 28 which forms the distal end of the balloon into the heating bath first.

The balloon formed in the mold is next cooled. One way to cool the balloon is to remove the mold 28 from the hot water bath 70 and place it in a cooling bath 72. As shown in FIG. 5, this step may be accomplished through use of a machine 60 having a pivot arm 74 capable of transferring the mold 28 from the hot 70 to the cold water bath 72. The cooling bath 72 is preferably maintained at 7–15° C. In the preferred embodiment, the balloon remains in the cooling bath 72 for approximately 10 seconds.

Finally, the ends of the tubing 13 extending from the mold 28 are cut off and the balloon is removed from the mold 28 by removing either the distal end 50 or proximal end 30 from the body section 40 of mold 28, then gently pulling the balloon from the remaining mold sections. To mount on a catheter 10, balloon 14 is cut at B and G and adhered to the catheter in conventional manner.

In another variation of the method using PET tubing, the tubing is first stretched uniformly at 90° C., then the tubing is cold stretched at room temperature. The cold stretching can be performed on one end or both ends. If it is performed on one end (distal end), the necked portion not stretched (proximal end) by cold drawing will form into the distal waist and partial cone portion during the blowing process, as described below.

Figure 8:
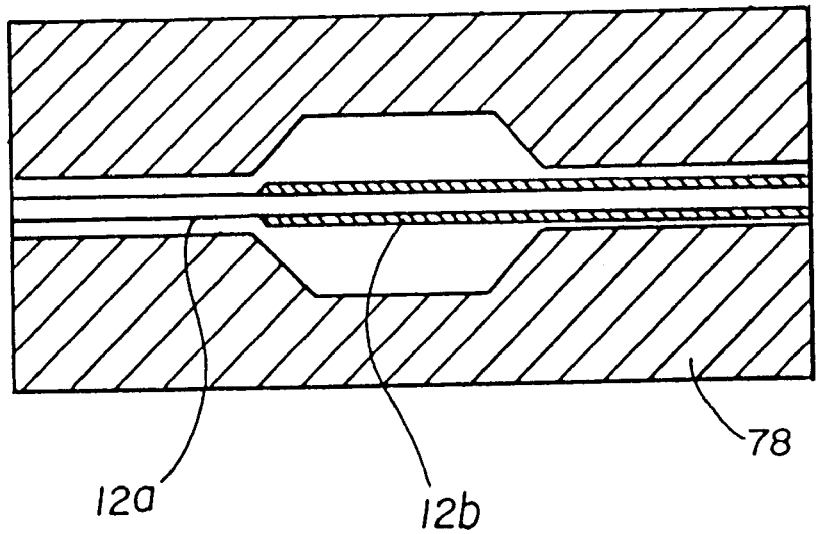
FIG. 8 is a side view of a drawn or stretched segment of tubing within a mold before the molding process according to an alternate embodiment of the invention.

A further variation of the method of the invention calls for drawing only one end, the proximal end, of the tubing or in other words, allowing the center portion 12b to remain at a greater length so that when the tubing is inserted into the mold, the center portion 12b extends out through the distal end of the mold as shown in FIG. 8. The remaining aspects of the procedure are unchanged. During the blowing process high pressure and high tension is maintained. The unstretched end as a result is forced out longitudinally taking the shape of the distal end of the mold and thus forming a distal cone portion.

The invention allows the distensible portion of a balloon to be correctly manufactured while providing small diameters at the proximal and distal ends thereof and substantially uniform thickness throughout. There is continuing need to reduce balloon and shaft profiles so that tighter arterial lesions may be crossed and treated. This invention allows for the formation of an uniform, thin-walled balloon having a flexible tapered end. The thinner, uniform walls and reduced diameters also allow tighter protector or compression sleeves to be installed over the balloon to further reduce its uninflated profile, allowing for easier passage into and across a stenosis. In the present invention the polymer tubing is not simultaneously drawn and expanded, in fact, the center portion 12b is appreciably not drawn at all. Constraint is used in both the stretching and molding processes so that the molecules of the wall material in the balloon region become stabilized. The balloon does extend axially slightly in the molding process, but only due to growth from the radial pressure and not due to stretching.

The various aspects of the invention are illustrated by the following non-limiting examples.

EXAMPLE 1

Pebax 7033 tube with dimensions ID (inner diameter) 0.0198"×OD (outer diameter) 0.0339" is cold-drawn at a very low temperature, approximately in the ranges of −100° C. to −20° C. A screw (or air) driven stretching machine with a pair of pneumatic grippers is used to stretch the tubing. The center portion is cooled under the glass transition temperature of the tubing material by directly spraying, liquid $N_2$ (Super Freeze may also be used) on the center portion (the cooling may also be accomplished by holding the center portion with cold clamps, in which case the temperature is predetermined). Ten sterilized balloons (3.0 mm in diameter and 20 mm in length) are made with a average double wall thickness 0.00143". The resulting burst pressure is 270–280 psi. The compliance is 8% at between 6 atm and 12 atm and 16% at between 6 atm and 16 atm.

EXAMPLE 2

PET tubing with dimensions ID 0.0189"×OD 0.0427" is cold-drawn in a water bath at 58° C. (below glass transition temperature) using the machine in Example 1 until unstretched length is 8 mm. Four unsterilized balloons measuring 3.5 mm in diameter and 20 mm in length and having an average double wall thickness of 0.00158" are tested. The resulting burst pressure is 400–410 psi and the compliance is 2.0% at between 6 atm and 12 atm and 3.2% at between 6 atm and 16 atm.

EXAMPLE 3

PET tubing with dimensions ID 0.0189"×OD 0.0427" is prestretched at 92° C. in a water bath for a 125% elongation, then is cold-drawn at room temperature using the machine in Example 1 until 10 mm unstretched length left. Four unsterilized balloons measuring 3.5 mm in diameter and 20 mm in length and having an average double wall thickness of 0.00111" are tested. The resulting burst pressure is 350 psi and the compliance is 2.3% at between 6 atm and 12 atm and 3.5% at between 6 atm and 16 atm.

EXAMPLE 4

Polyester elastomer tubing with dimensions ID 0.0179"×OD 0.0270" is cold stretched at room temperature using the machine in Example 1 until unstretched length is 8 mm. Ten sterilized balloons measuring 1.5 mm in diameter and 20 mm in length and having an average double wall thickness of 0.0019" are tested. The resulting burst pressure is 250–260 psi and the compliance is 33.6% at between 6 atm and 12 atm and 99.3% at between 6 atm and 16 atm.

EXAMPLE 5

Nylon 12 tubing with dimensions ID 0.0182"×OD 0.0254" is cold stretched at room temperature using the machine in Example 1 until unstretched length is 10 mm. Four unsterilized balloons measuring 2.0 mm in diameter and 20 mm in length and having an average double wall thickness of 0.00088" are tested. The resulting burst pressure is 270–280 psi and the compliance is 9.5% at between 6 atm and 12 atm and 16.7% at between 6 atm and 16 atm.

EXAMPLE 6

PET tubing with dimensions ID 0.0226"×OD 0.0470" is stretched at 90° C. to a stretch ratio of 2.25 at a speed of 0.53 inch/sec. The tubing is then necked by cold-drawing the distal end at room temperature using the method in Example 3 and at a speed of 0.4 inch/sec to a draw ration of 1.18 to form the resulting balloon's distal waist and cone portion. Four balloons are made and tested. The balloon size is 3.5 mm in diameter and 20 mm in length. The balloon double wall thickness is about 0.00148". As a result of cold-drawing, the wall thickness of the cone portion is measurably reduced and the wall thickness of the waist portion is reduced by about 50% compared to balloons manufactured without cold-drawing. The resulting burst pressure is 338 psi.

EXAMPLE 7

PET tubing with dimensions ID 0.0226"×OD 0.0470" is stretched at 90° C. to a stretch ratio of 2.25 at a speed of 0.53 inch/sec. The tubing is then necked by cold-drawing the distal and proximal ends at room temperature using the method in Example 3 and at a speed of 0.4 inch/sec to a draw ratio of 1.18 to form the resulting balloon's distal and proximal waist and cone portions. Four balloons are made and tested. The balloon size is 3.5 mm in diameter and 20 mm in length. The balloon double wall thickness is about 0.00148". As a result of cold-drawing, the wall thickness of the cone portions are measurably reduced and the wall thickness of the waist portions are reduced by about 50% compared to balloons manufactured without cold-drawing. The resulting burst pressure is 338 psi.

EXAMPLE 8

Balloons with 3.50 mm in diameter and 20 mm in length are made by the method described in example 6 and are assembled on catheters. The deflated distal balloon profile is 0.033 inch compared to a catheter made from balloons without the necking process of the present invention which has a deflated distal balloon profile of 0.040 inch.

EXAMPLE 9

Balloons are made by the method in Example 6 having a 4.0 mm diameter and assembled on catheters. The resulting deflated distal balloon profile is 0.035 inch as compared to a profile of 0.045 of balloon catheters made from conventional methods.

EXAMPLE 10

The balloons in Example 1 are assembled on catheters. The deflated distal balloon profile is 0.031 inch. The profile of balloons made without cold stretching or necking resulted in a deflated distal balloon profile in the range of 0.036 to 0.041 inch.

The resulting balloons of the above Examples display not only reduced balloon thickness, but reduced cone and waist thicknesses, thus producing a balloon having a reduced profile and greatly simplifying the insertion into the body.

What is claimed is:

1. A method of making a balloon for a catheter device, comprising the steps:
   extruding a segment of thermoplastic material having a predetermined wall thickness and length, the segment having a proximal end, a distal end and a center portion;
   drawing the segment to a predetermined length while maintaining the temperature of the segment below the glass transition temperature of the thermoplastic material, or below the highest glass transition temperature if the material is a block copolymer, wherein the proximal end forms a first waist; and
   expanding the segment having a first waist in a mold to produce the balloon, the balloon having a body portion, wherein the center portion of said segment becomes the balloon body portion.

2. The method as in claim 1, wherein the thermoplastic material is chosen from the group consisting of polyamide elastomers, polyester elastomers, polyamides, polyesters, polyethylenes, polyurethanes, polyethylene ionomers, and ethylene vinyl acetates.

3. The method as in claim 2, wherein the thermoplastic material is polyethylene terephthalate.

4. The method as in claim 2, wherein in the drawing step the distal end of the segment forms a second waist and the segment is expanded having a first and second waist and wherein during the drawing step the segment is maintained at a temperature of no more than approximately room temperature.

5. The method as in claim 4, wherein the center portion is cooled just prior to drawing, such that the center portion remains cool during the drawing step.

6. The method as in claim 5, wherein the stretch rate is between 25% to 75% per second.

7. The method as in claim 6, wherein the segment is allowed to reach approximate room temperature before the expanding step.

8. The method as in claim 7, the expanding step comprising placing the segment of a thermoplastic material in the mold and blowing the balloon by pressurizing and tensioning the segment and gradually dipping the mold into a heated heat transfer media so as to sequentially blow the proximal end, the center portion and the distal end of the balloon, the segment being subjected to a relatively lower pressure than while the first waist and second waist portions are blown.

9. The method as in claim 8, wherein the segment is also subjected to a relatively a lower tension while the body portion is blown than while the first waist and second waist portions are blown.

10. The method as in claim 7, wherein the expanding step comprises the steps of placing the stretched segment in a mold having an internal form corresponding to the desired outer configuration of the balloon, and blowing the balloon by applying axial tension and internal pressure to the preform upon dipping of the mold into a heated heat transfer media, the expanding step further comprising:
   pressurizing the stretched segment to a first pressure in the range of 150–320 psi and applying a first tension in the range of 5–150 g;
   dipping the mold to a first depth in the range of from the transition (C) from the first waist to the first cone to the transition (D) from the first cone to the body portion of the balloon;
   reducing the pressure to a second pressure between 80 and 170 psi and setting a second tension in the range of the first tension;
   dipping the mold to a second depth in the range of from the transition (E) from the body portion to the second cone portion to the transition (F) from the second cone to the second waist;
   increasing the pressure to a third pressure higher than the second pressure and between 150 and 320 psi and increasing the tension to a third tension, higher than the first tension, and then,
   dipping the mold to a third depth (H) beyond the depth of the second waist.

11. The method as in claim 10 wherein the third tension is in the range of 50 to 700 g.

12. The method as in claim 10 wherein:
the mold is held at the first depth for a predetermined first time interval while maintaining said first tension and first pressure before said pressure reducing step;
the mold is held at the second depth while maintaining the second tension and the second pressure for a predetermined second time interval before said pressure increasing step; and,
the mold is held at the third depth for a predetermined third time interval while maintaining said third tension and third pressure.

13. The method of claim 12, wherein said heat transfer media is heated to a temperature of 90° C. to 100° C.

14. The method of claim 10, wherein the second tension is the same as the first tension.

15. The method of claim 10, wherein the second tension is less than the first tension.

16. The method as in claim 5, wherein the stretch rate is approximately 75% per second.

17. The method as in claim 5, wherein the cooling is accomplished by clamping the center portion with cold clamps, such that the center portion remains cool during the drawing step.

18. The method as in claim 4, wherein the segment is cooled just prior to drawing.

19. The method as in claim 1 wherein during the drawing step the center portion is further cooled relative to the proximal and distal ends.

20. A method of making a balloon for a catheter device, comprising the steps:
extruding a segment of thermoplastic material, the segment having a proximal end, a distal end and a center portion;
maintaining the segment at a temperature below the glass transition temperature of the thermoplastic material or below the highest glass transition temperature if the material is a block copolymer;
drawing the proximal end to a predetermined length while maintaining the segment below said glass transition temperature, wherein the proximal end forms a first waist; and
expanding the segment having a first waist in a mold to produce the balloon, the balloon having a body portion, wherein the center portion of said segment becomes the balloon body portion, and the distal end, due to expansion in the mold, stretching longitudinally to form a second waist.

21. A method of making a balloon for a catheter device, comprising the steps:
extruding a segment of thermoplastic material, the segment having a proximal end, a distal end and a center portion;
cooling the segment to a temperature below the glass transition temperature of the material;
drawing the segment while maintaining the temperature of the center portion, below the glass transition temperature of the material, wherein, during the drawing, the proximal and distal ends form a first and second waist, respectively; and
expanding the segment having a first and second waist in a mold to produce the balloon, the balloon having a body portion, wherein the center portion of said segment becomes the balloon body portion.

22. The method of claim 21 including the additional step of cooling the center portion relative to the proximal and distal ends before or during the drawing step.

23. A method of making a balloon for a catheter device, comprising the steps:
extruding a segment of thermoplastic material, the segment having a proximal end, a distal end and a center portion;
cooling the segment to a temperature below the glass transition temperature of the material;
drawing the proximal end to a predetermined length while maintaining the temperature of the segment below the glass transition temperature of the material, wherein, during the drawing, the proximal end forms a first waist; and
expanding the segment having a first waist in a mold to produce the balloon, the balloon having a body portion, wherein the center portion of said segment becomes the balloon body portion, and the distal end, due to expansion in the mold, stretching longitudinally to form a second waist.

24. The method of claim 23 including the additional step of cooling the center portion relative to the proximal and distal ends before or during the drawing step.

* * * * *